United States Patent [19]
Bencherif et al.

[11] Patent Number: 5,811,442
[45] Date of Patent: Sep. 22, 1998

[54] PHARMACEUTICAL COMPOSITIONS FOR THE TREATMENT OF CONDITIONS ASSOCIATED WITH DECREASED BLOOD FLOW

[76] Inventors: Merouane Bencherif, 1140 Lazyboy La., Winston-Salem, N.C. 27103; Patrick Michael Lippiello, 1233 Arboretum Dr., Lewisville, N.C. 27023

[21] Appl. No.: 804,224

[22] Filed: Feb. 21, 1997

[51] Int. Cl.⁶ ............................. A01N 43/64; A61K 31/44
[52] U.S. Cl. .............................................................. 514/384
[58] Field of Search ................................................ 514/384

[56] References Cited

U.S. PATENT DOCUMENTS

| | | | |
|---|---|---|---|
| 5,212,188 | 5/1993 | Caldwell et al. | 514/343 |
| 5,585,388 | 12/1996 | Cosford et al. | 514/343 |
| 5,597,919 | 1/1997 | Dull et al. | 544/242 |
| 5,604,231 | 2/1997 | Smith et al. | 514/256 |
| 5,616,707 | 4/1997 | Crooks et al. | 544/242 |
| 5,616,716 | 4/1997 | Dull et al. | 546/300 |

FOREIGN PATENT DOCUMENTS

WO96/20600   7/1996   WIPO.

OTHER PUBLICATIONS

Bencherif et al., "RJR–2403: A Nicotine Agonist with CNS Selectivity I. In Vivo Characterization", J. of Pharmacology and Exper. Therapeutics, 279(3):1413–1421 (1996).

Henrich et al.; "Microcirculatory Effects of Nicotine and Related Alkaloids"; Klin Wochenschr, 62(Suppl II): 92–100 (1984).

Wilson, Jr. et al.; "Nicotine–Like Actions of cis–Metanicotine and trans–Metanicotine"; J. of Pharmacology and Exper. Therapeutics, 196(3):685–696 (1976).

LaForge, "The Preparation and Properties of Some New Derivatives of Pyridine"; J. Amer. Chem. Soc. 50:2477–2483 (1928).

Acheson et al.; "Transformations involving the Pyrrolidine Ring of Nicotine"; J. Chem. Soc., Perkins Trans., 1:579–585 (1980).

Bencherif et al.; "RJR–2403: A Nicotine Agonist with CNS Selectivity I. In Vitro Characterization"; J. of Pharmacology and Exper. Therapeutics, 279(3):1413–1421 (1996).

Lippiello et al.; "RJR–2403: A Nicotine Agonist with CNS Selectivity II. In Vivo Characterization"; J. of Pharmacology and Exper. Therapeutics, 279(3):1422–1429 (1996).

Jinno et al.; "Nicotine and acetylcholine induce release of calcitonin gene–related peptide from rat trachea"; Amer. Physiological Soc., 1651–1656 (1994).

*Primary Examiner*—Russell Travers
*Assistant Examiner*—Dwayne C. Jones

[57] ABSTRACT

Patients suffering from or susceptible to conditions of the vascular or circulatory system, particularly the microvasculature, which conditions are associated with decreased blood flow in regions of microcirculation (e.g., Raynaud's disease and Raynaud's phenomenon) are treated with pharmaceutical compositions incorporating an effective amount of an aryl substituted olefinic amine compound. The compounds incorporated into the pharmaceutical compositions of the present invention exhibit selective activity of to the β2-containing nicotinic acetylcholine receptors and thereby yield beneficial therapeutic effects increasing vascular blood flow in regions of microcirculation.

46 Claims, No Drawings

PHARMACEUTICAL COMPOSITIONS FOR THE TREATMENT OF CONDITIONS ASSOCIATED WITH DECREASED BLOOD FLOW

BACKGROUND OF THE INVENTION

The present invention relates to compounds having pharmaceutical properties, and in particular to compounds useful for treating conditions of the vascular or circulatory system. More specifically, the present invention relates to methods for treating patients having conditions of the microvasculature, which conditions are characterized by decreased blood flow in regions of microcirculation. In addition, the present invention relates to compositions of matter useful as pharmaceutical compositions for the prevention and treatment of such conditions.

In the human vascular or circulatory system, blood is supplied throughout the body so as to provide oxygen and nutrient requirements to body tissues. Quite simply, blood flows from the heart, through the arteries, through capillaries, and through veins back to the heart. Those regions where capillaries are located and in which blood flows through those capillaries are referred to as the "microvasculature," and the movement of blood flow through each region is referred to as "microcirculation."

Blood flows through cerebral regions, in addition to the so-called "peripheral" regions. Under normal circumstances, well regulated blood flow in cerebral regions in maintained. See, TEXTBOOK OF PHYSIOLOGY, edit. by Berne and Levy (1983). However, cerebral regions are very sensitive to conditions such as ischemia. Regulatory mechanisms, neural factors and carbon dioxide tension cell contribute to cerebral vascular tone.

Capillaries vary in their diameter and in density of distribution throughout the body. Blood flow rates in the capillaries are not uniform, with constriction and dilation being types of vasomotion which affect those blood flow rates. Typically, such blood flow rates are controlled by a variety of homeostatic physiological processes, with vasomotion regulated by intrinsic control (e.g., levels of lactic acid, carbon dioxide, or hydrogen ion), extrinsic mechanisms (e.g., sympathetic and parasympathetic neural influences) and humoral factors (e.g., release of renin-angiotensin, kinins, serotonin, histamine, protacyclins, neuropeptides, and atrial natuiretic factors).

When vasoconstriction occurs, particularly in regions of the microvasculature, normal blood flow in those affected regions is significantly reduced, often resulting in undesirable conditions. See Cecil Textbook of Medicine 19th ed. p.147–368 (1988). There are numerous vascular conditions associated with a restriction of blood flow (relative to normal blood flow), particularly in those regions associated with microcirculation. Such conditions typically affect regions of the vascular system located relatively distant from the heart (i.e., the extremities including the hands, feet, fingers, and toes). Exemplary vascular conditions include occlusive arterial disease, impotence, connective tissue disease, ischemic conditions, Raynaud's phenomenon and Raynaud's disease. Raynaud's phenomenon is characterized by episodic digital ischemia, manifested by the sequential development of digital blanching, cyanosis, and rubor of the fingers or toes following cold exposure and subsequent rewarming. The etiology of Raynaud's phenomenon is not presently known, but it has been believed to be an abnormal response of the vascular smooth muscle. Vasoconstriction and reduced blood flow can result from non-disease conditions as well, including vascular injury, physical or chemical injury, neurogenic factors, and various neuropathies. In addition, decreased or restricted blood flow in the microvasculature is an important concern when promotion of wound healing is desired, such as during broken bone repair and following surgery (e.g., following limb or digit reattachment, when restricted or decreased blood flow may result in further trauma or failure of reattachment).

There are various manners of treatment for vascular diseases and conditions associated with decreased blood flow in the extremities. Such treatments depend upon the etiology and severity of the symptoms exhibited by each individual patient. Calcium antagonists (e.g., nifedipine, diltiazem), alpha-adrenergic receptor blockers (e.g., phenoxybenzamine, tolazoline, prazosin), drugs that interfere with sympathetic nerve activity (e.g., reserpine, guanethidine, alpha-methyldopa), and vasodilators (e.g., PGE1, PGE2, PGI2, iloprost, misoprostol) represent the spectrum of drugs currently in use or under investigation for the treatment of the various vascular diseases. See Cecil Textbook of Medicine, 19th ed. pp. 355–368 (1988).

Nicotinic acetylcholine receptors represent a heterogeneous family of ligand gated ion channels in the central nervous system (CNS) and peripheral nervous system (PNS) tissues of mammalian species. See, Lukas and Bencherif, *International Review Neurobiol.* 34:25 (1992); Arneric et al., *Exp. Opin. Invest. Drugs* 5(1):79–100 (1996); Baron et al. *SRNT Newsletter* 1(4):3 (1995); Williams et al. DN&P 7(4):205–223 (1994). Certain of these receptors, upon activation, result in affecting changes to the vascular system. In particular, activation of certain nicotinic acetylcholine receptors results in vasoconstriction, while activation of certain other nicotinic acetylcholine receptors results in vasodilation. Nicotinic compounds reportedly have neuroprotective effects and enhance cortical cerebral blood flow. Decker et al., *J. Pharm. & Exper. Therapeutics* 270(1):319 (1994).

Certain nicotinic cholinergic agonists provide affects upon the vascular system. Okamura and Toda, *Euro. J Pharmacol.* 263:85 (1994). Henrich et al., *Klin. Wochenschr* 62:92 (1984). In addition, neurogenic relaxation reportedly occurs upon release of endogenous peptides which release is enhanced by administration of nicotinic cholinergic agonists. See, Jinno et al., *Applied Physiol.* 76:1651 (1994). However, certain agonists (e.g., nicotine) do not discriminate between the various nicotinic acetylcholine receptor subtypes expressed in structures involved in the control of vascular tone (i.e., such agonists are not selective with regard to binding and activation of various receptor subtypes, while other nicotinic agonists exhibit selectivity). See, Bencherif et al., *JPET* 279:1413 (1996).

It would be desirable to provide a pharmaceutical composition useful for the treatment of vascular conditions, particularly those conditions affecting the microvasculature. It would be desirable to provide a pharmaceutical composition incorporating a compound which interacts with nicotinic acetylcholine receptors which have the potential to affect vasodilation, but which compound does not significantly affect those receptors which have the potential to induce vasoconstriction. As such, it would be desireable to provide a method for providing an effect upon the vascular system, which effect favors promotion of vasodilation over vasoconstriction. Accordingly, it is desirable to provide a pharmaceutical composition capable of producing beneficial effects upon the circulatory system (e.g., suitable for treating vascular conditions associated with decreased or restricted blood flow, particularly in regions of the microvasculature).

SUMMARY OF THE INVENTION

As a first aspect, the present invention relates to a method for providing a beneficial effect upon the vascular or circulatory system, and hence for providing treatment of conditions of the vascular or circulatory system. In particular, the present invention relates to methods for providing treatment for conditions associated with decreased blood flow in the circulatory system, and as such relates to methods for eliciting vasodilation. More specifically, the method relates to treatment of such conditions and eliciting vasodilation, particularly in the microvasculature. The method involves administering to a subject, an aryl substituted olefinic amine compound (e.g., pyrimidinyl substitutued olefinic amine or pyridinyl substituted olefinic amine compounds). The route of administration and amount administered is such that the subject receives the compound in a dose effective to cause prevention or improvement of the condition (e.g., by causing a net increase in vasodilation over vasoconstriction).

In another aspect, the present invention relates to a pharmaceutical composition comprising an effective amount of a compound of the present invention. The pharmaceutical composition includes a compound which is a therapeutic agent for the treatment of conditions of the circulatory system, in particular the microvasculature, which conditions are characterized by restricted or decreased blood flow. The pharmaceutical composition, when administered to a subject in need thereof, acts to favor vasodilation over vasoconstriction, particularly in the microvasculature.

The pharmaceutical compositions of the present invention are useful for the treatment of conditions of the vascular or circulatory system, and particularly the microvasculature. The pharmaceutical compositions (when administered in effective amounts) provide therapeutic benefit to individuals suffering from the effects of vasoconstriction or otherwise conditions of the microvasculature which are characterized by decreased blood flow in the microvasculature. The compounds within those compositions have the potential to exhibit selective nicotinic pharmacology, and thereby promote vasodilation or improve blood flow in regions of restricted blood flow. The pharmaceutical compositions of the present invention are believed to be safe and effective with regard to the treatment of conditions of the circulatory system associated with decreased blood flow.

DETAILED DESCRIPTION OF THE INVENTION

The compounds of the present invention, which are selective to the β2 containing nicotinic acetylcholine receptors, include compounds of the Formula I:

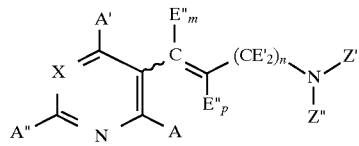

where X is nitrogen or carbon bonded to a substituent species characterized as having a sigma m value greater than 0, often greater than 0.1, and generally greater than 0.2, and even greater than 0.3; less than 0 and generally less than −0.1; or 0; as determined in accordance with Hansch et al., $Chem. Rev.$ 91:165 (1991); n is an integer which is 1, 2, 3, 4, 5, 6, 7, or 8, preferably is 1, 2, or 3, and most preferably is 2 or 3; E' represents hydrogen or lower alkyl (e.g., straight chain or branched alkyl including $C_1$–$C_8$, preferably $C_1$–$C_5$, such as methyl, ethyl, or isopropyl) or halo substituted lower alkyl (e.g., straight chain or branched alkyl including preferably $C_1$–$C_8$, preferably $C_1$–$C_5$, such as trifluoromethyl or trichloromethyl), but preferably is H; E" represents lower alkyl (e.g., straight chain or branched alkyl including preferably $C_1$–$C_8$, preferably $C_1$–$C_5$, such as methyl, ethyl, or isopropyl) or halo substituted lower alkyl (e.g., straight chain or branched alkyl including $C_1$–$C_8$, preferably $C_1$–$C_5$, such as trifluoromethyl or trichloromethyl); Z' and Z" individually represent hydrogen or lower alkyl (e.g., straight chain or branched alkyl including $C_1$–$C_8$, preferably $C_1$–$C_5$, such as methyl, ethyl, or isopropyl), and preferably at least one of Z' and Z" is hydrogen, and most preferably Z' is hydrogen and Z" is methyl; alternatively Z' is hydrogen and Z" represents a ring structure (cycloalkyl or aromatic), such as cyclopropyl, cyclobutyl, cyclopentyl, cyclohexyl, cycloheptyl, adamantyl, quinuclidinyl, pyridinyl, quinolinyl, pyrimidinyl, phenyl, or benzyl (where any of the foregoing can be suitably substituted with at least one substituent group, such as alkyl, halo, or amino substituents); alternatively Z', Z", and the associated nitrogen atom can form a ring structure such as aziridinyl, azetidinyl, pyrollidinyl, piperidinyl, piperazinyl, or morpholinyl; A, A' and A" individually represent hydrogen, halo (e.g., F, Cl, Br, or I), alkyl (e.g., lower straight chain or branched $C_1$–$C_8$ alkyl, but preferably methyl or ethyl), or NX"X''' where X" and X''' are individually hydrogen or lower alkyl, including $C_1$–$C_8$, preferably $C_1$–$C_5$ alkyl; m is 0 or 1, preferably 0; p is 0 or 1, preferably 0; the wavy line in the structure represents a cis (Z) or trans (E) form of the compound. As will be clear to those skilled in the art, when m or p is 0, E" is not present and H fills the valence of the carbon atom on which E" is positioned. More specifically, X includes N, C—H, C—F, C—Cl, C—Br, C—I, C—R', C—NR'R", C—$CF_3$, C—OH, C—CN, C—$NO_2$, C—$C_2$R', C—SH, C—$SCH_3$, C—$N_3$, C—$SO_2CH_3$, C—OR', C—SR', C—C(=O)NR'R", C—NR'C(=O)R', C—C(=O)R', C—C(=O)OR', C($CH_2$)$_q$OR', C—OC(=O)R', COC(=O)NR'R" and C—NR'C(=O)OR' where R' and R" are individually hydrogen or lower alkyl (e.g., $C_1$–$C_{10}$ alkyl, $C_1$–$C_5$ alkyl, and more preferably methyl, ethyl, isopropyl or isobutyl), an aromatic group-containing species or a substituted aromatic group-containing species, and q is an integer from 1 to 6. R' and R" can be straight chain or branched alkyl, or R' and R" can form a cycloalkyl functionality (e.g., cyclopropyl, cyclobutyl, cyclopentyl, cyclohexyl, cycloheptyl, adamantyl, quinuclidinyl. Representative aromatic group-containing species include pyridinyl, quinolinyl, pyrimidinyl, phenyl, benzyl, (where any of the foregoing can be suitably substituted with at least one substituent group, such as alkyl, halo, or amino substituents. Representative aromatic ring systems are set forth in Gibson et al., $J. Med. Chem.$ 39:4065 (1996). When X represents a carbon atom bonded to a substituent species, that substituent species often has a sigma m value which is between about −0.3 and about 0.75, and frequently between about −0.25 and about 0.6. In certain circumstances the substituent species is characterized as having a sigma m value not equal to 0. In addition, it is highly preferred that A is hydrogen, it is preferred that A' is hydrogen, and normally A" is hydrogen. Generally, both A and A' are hydrogen; sometimes A and A' are hydrogen, and A" is amino, methyl or ethyl; and often A, A' and A" are all hydrogen. Depending upon the identity and positioning of E', certain compounds can be optically active. Typically, the values of each of m and p, and the selection of E', are such that up to about 4, and frequently up to 3, of the substituents designated as E' and E" are non-hydrogen substituents (i.e., substituents such as lower alkyl or halo-substituted lower alkyl).

Of particularly interest are compounds of Formula I where n, m, p, X, A, A', A", E', E", Z', and Z" are as defined hereinbefore, and those compounds can have the cis (Z) or trans (E) form. For such compounds of particular interest, X most preferably is nitrogen or carbon bonded to a substituent species characterized as having a sigma m value greater than 0, often greater than 0.1, generally greater than 0.2, and even greater than 0.3; less than 0 and generally less than −0.1; or 0. More specifically, the compounds of particular interest are those compounds wherein X is CH; C—Br; C—O(CH$_2$)$_q$R', and R' is an aromatic species, particularly phenyl; C—O—R' where R' is an aromatic ring, particularly phenyl; C—O—R' where R' is an alkyl, particularly isopropyl or ethyl; C—COR' where R' is methyl.

One representative compound is (E)-4-(5-pyrimidinyl)-3-buten-1-amine for which X is N, E' is H, n is 2, m is 0, p is 0, and A, A', A", Z' and Z" each are hydrogen. Another representative compound is (E)-4-[3-(5-methoxypyridin)yl] 3-buten-1-amine for which X is C—OR' where R' is methyl, E' is H, n is 2, m is 0, p is 0, and A, A', A", Z' and Z" each are hydrogen. Another representative compound is (E)-N-methyl-4-(5-pyrimidinyl)-3-buten-1-amine for which X is N, E' is H, n is 2, m is 0, p is 0, A, A', A", and Z' are each hydrogen, and Z" is methyl. Another representative compound is (E)-N-methyl-4-[3-(5-methoxypyridin)yl]-3-buten-1-amine for which X is C—OR' where R' is methyl, E' is H, n is 2, m is 0, p is 0, A, A', A", and Z' are each hydrogen, and Z" is methyl. Another representative compound is (E)-N-methyl-4-[3-(5-ethoxypyridin)yl]-3-buten-1-amine for which X is C—OR' where R' is ethyl, E' is H, n is 2, m is 0, p is 0, A, A', A" and Z' each are hydrogen, and Z" is methyl. Another representative compound is (E)-N-methyl-4-[3-(5-aminopyridin)yl]-3-buten-1-amine for which X is C—NR'R" where each of R' and R" are H, E' is H, n is 2, m is 0, p is 0, A, A', A" and Z' each are hydrogen, and Z" is methyl. Another representative compound is (E)-N-methyl-4-[3-(5-bromopyridin)yl]-3-buten-1-amine for which X is C—Br, E' is H, n is 2, m is 0, p is 0, A, A', A" and Z' each are hydrogen, and Z" is methyl. Another representative compound is (E)-N-methyl-4-[3-(6-methylpyrindin)yl]-3-buten-1-amine for which X is C—H, E' is H, n is 2, m is 0, p is 0, A" is methyl, and A, A' Z', and Z" are each hydrogen. Another representative compound is (E)-4-(5-pyrimidinyl)-3-buten-1-amine for which X is N, E' is H, n is 2, m is 0, p is 0, and A, A', A" Z' and Z" are each hydrogen. Another representative compound is (E)-N-methyl-4-[3-(5-benzyloxypyridin)yl]-3-buten-1-amine for which X is C—OR'R" where R' is alkylene, particularly methylene and R" is an aromatic ring, particularly benzyl or phenyl, E' is H, n is 2, m is 0, p is 0, and A, A', A", and Z' are each H, and Z" is methyl. Another representative compound is (E)-4-[3-(5-bromopyrdin)yl]-3-buten-1-amine for which X is C—Br, E' is H, n is 2, m is 0, p is 0, and A, A', A", Z' and Z" are each H. Another representative compound is (E)-N-methyl-4-[3-(5-phenoxypyridin)yl]-3-buten-1-amine for which X is C—OR'where R' is an aromatic ring particularly phenyl, E' is H, n is 2, m is 0, p is 0, and A, A', A", and Z' are each H and Z" is methyl. Another representative compound is (E)-N-methyl-4-[3-(5-isopropoxypyridin)yl]-3-buten-1-amine for which X is C—OR'where R' is isopropyl, E' is H, n is 2, m is 0, p is 0, A, A', A", and Z' are each H, and Z' is methyl. Another representative compound is (E)-N-methyl-4-[3-(5-methoxymethylpyridin)yl-3-buten-1-amine for which X is C—CH$_2$—OCH$_3$, E' is H, n is 2, m is 0, p is 0, A, A', A", and Z' are each H, and Z" is methyl. Another representative compound is (E)-N-methyl-4-[3-(5-phenylpyridin)yl]-3-buten-1-amine for which X is C—R' where R' is phenyl, E' is H, n is 2, E" is H, m is 0, p is 0, A, A', A", and Z' are each H, and Z" is methyl. Another representative compound is (E)-4-(3-pyridinyl)-3-buten-1-amine for which X is CH, E' is H, n is 2, m is 0, p is 0, and A, A', A", Z' and Z" are each H. Another representative compound is (E)-4-[3-(5-ethoxypyridin)yl]-3-buten-1-amine for which X is C—OR'where R' is ethyl, E' is H, n is 2, m is 0, p is 0, A, A', A", Z' and Z" are each H. Another representative compound is (E)-N-methyl-5-(3-pyridinyl)-4-penten-2-amine for which X is CH$_2$, one E' is methyl and all other E' are H, n is 3, m is 0, p is 0, A, A', A", and Z' are each H, and Z" is methyl. Another representative compound is (E)-N-methyl-4-[3–5-(ethylthiopyridinyl)]-3-buten-1-amine for which X is C—S—C$_2$H$_5$, E' is H, n is 2, m is 0, p is 0, and A, A', A" and Z' are each H and Z" is methyl. Another representative compound is (E)-N-methyl-4-[3–5-acetamidopyridinyl]-3-buten-1-amine for which X is C—NH—C(=O)—CH$_3$, E' is H, n is 2, m is 0, p is 0, and A, A', A" and Z' are each H and Z" is methyl. Another representative compound is (E)-N-methyl-4-[3–5-carbamoyl-pyridinyl]-3 -buten-1-amine for which X is C—C(=O)—NH$_2$, E' is H, n is 2, m is 0, p is 0, and A, A', A" and Z' are each H and Z" is methyl.

The manner in which aryl substituted olefinic amine compounds of the present invention are provided can vary. (E)-metanicotine can be prepared using the techniques set forth by Löffler et al., *Chem. Ber.* 42:3431 (1909) and Laforge, *J.A.C.S.* 50:2477 (1928). Certain novel 6-substituted metanicotine-type compounds can be prepared from the corresponding 6- substituted nicotine-type compounds using the general methods of Acheson et al., *J. Chem. Soc., Perkin Trans.* 1 2:579 (1980). The requisite precursors for such compounds, i.e., 6-substituted nicotine-type compounds, can be synthesized from 6-substituted nicotinic acid esters using the general methods disclosed by Rondahl, *Acta Pharm. Suec.* 14:113 (1977). Preparation of certain 5-substituted metanicotine-type compounds can be accomplished from the corresponding 5-substituted nicotine-type compounds using the general method taught by Acheson et al., *J. Chem. Soc., Perkin Trans.* 1 2:579 (1980). The 5-halo nicotine-type compounds and the 5-amino nicotine-type compounds can be prepared using the general procedures disclosed by Rondahl, *Act. Pharm. Suec.* 14:113 (1977). The 5-trifluoromethyl nicotine-type compounds can be prepared using the techniques and materials set forth in Ashimori et al., *Chem. Pharm. Bull.* 38(9):2446 (1990) and Rondahl, *Acta Pharm. Suec.* 14:113 (1977). Certain metanicotine-type compounds (e.g., 3-(5-phenylpyridiny)yl-3-alkene-amine type compounds) can be prepared using the types of synthetic methodologies set forth in Miyaura et al., *Synth. Commun.* 11:513 (1981) and U.S. Pat. No. 5,409,920 to Guthikonda et al. Furthermore, preparation of certain metanicotine-type compounds can be accomplished using a palladium catalyzed coupling reaction of an aromatic halide and a terminal olefin containing a protected amine substituent, removal of the protective group to obtain a primary amine, and optional alkylation to provide a secondary or tertiary amine. In particular, certain metanicotine-type compounds can be prepared by subjecting a 3-halo substituted, 5-substituted pyridine compound or a 5-halo substituted pyrimidine compound to a palladium catalyzed coupling reaction using an olefin possessing a protected amine functionality (e.g., an olefin provided by the reaction of a phthalimide salt with 3-halo-1-propene, 4-halo-1-butene, 5-halo-1pentene or 6-halo-1-hexene). See, Frank et al., *J. Org. Chem.* 43(15):2947 (1978) and Malek et al., *J.*

*Org. Chem.* 47:5395 (1982). Alternatively, certain metanicotine-type compounds can be prepared by coupling an N-protected, modified amino acid residue, such as 4-(N-methyl-N-tert-butyloxycarbonyl)amino-butyric acid methyl ester, with an aryl lithium compound, as can be derived from a suitable aryl halide and butyl lithium. The resulting N-protected aryl ketone is then chemically reduced to the corresponding alcohol, converted to the alkyl halide, and subsequently dehydrohalogenated to introduce the olefin functionality. Removal of the N-protecting group affords the desired metanicotine-type compound.

There are a number of different methods for providing (Z)-metanicotine-type compounds. In one method, (Z)-metanicotine-type compounds can be synthesized from nicotine as a mixture of the E and Z isomers; and the (Z)-metanicotine-type compounds can then be separated by chromatography using the types of techniques disclosed by Sprouse et al., Abstracts of Papers, p.32, Coresta/TCRC Joint Conference (1972). In another method, (Z)-metanicotine can be prepared by the controlled hydrogenation of the corresponding acetylenic compound (e.g., N-methyl-4-(3-pyridinyl)-3-butenylamine). For example, certain 5-substituted (Z)-metanicotine-type compounds and certain 6-substituted (Z)-metanicotine-type compounds can be prepared from 5-substituted-3-pyridinecarboxaldehydes and 6-substituted-3-pyridinecarboxaldehydes, respectively.

Representative compounds of the present invention, representative starting materials, and methods of synthesizing representative compounds and suitable salts thereof are set forth in U.S. Pat. No. 5,597,919 to Dull et al.; U.S. patent application Ser. No. 08/631,762; U.S. patent application Ser. No. 08/635,165; and PCT No. WO 96/31475.

One representative compound, (E)-N-methyl-4-(3-[5-(ethylthio)pyridinyl])-3-buten-1-amine is prepared from N-methyl-N-(tert-butoxycarbonyl)-3-buten-1-amine and 3-bromo-5-(ethylthio)pyridine using the techniques set forth in W.C. Frank, et al.,*J. Org. Chem.* 43(15):2947 (1978), and the tert-butoxy carbonyl protecting group is subsequently removed. Specifically, N-methyl-N-(tert-butoxycarbonyl)-3-buten-1-amine is prepared by (i) reacting 4-bromo-1-butene at 0.035 mole scale with a ten fold excess of condensed methylamine in N,N-dimethylformamide solvent in the presence of potassium carbonate to provide a 97% yield of N-mehtyl-3-buten-1-amine; (ii) the amine thus prepared is reacted at 0.030 mole scale with one equivalent of di-tert-butyldicarbonate in tetrahydrofuran to give N-methyl-N-(tert-butoxycarbonyl)-3-buten-1-amine in 68% yield. The 3-bromo-5-(ethylthio)pyridine is produced by the reaction of sodium ethanethiolate on 3,5-dibromopyridine in N,N-dimethylformamide in 86% yield. N-methyl-N-(tert-butoxycarbonyl)-3-buten-1-amine and 3-bromo-5-(ethylthio)pyridine are reacted using the Heck reaction on a 1.6 mmole scale in 2:1 acetonitrile:triethylamine using a catalyst consisting of one mole percent palladium acetate and four mole percent tri-o-tolylphosphine. N-methyl-N-(tert-butoxycarbonyl)-4-(3 -[5 -(ethylthio)pyridinyl])-3 -buten- 1-amine is obtained in 59% yield. Deprotection of the product may then be accomplished by 1:1 6N hydrochloric acid:tetrahdyrofuran.

Other representative compounds include (E)-N-methyl-4-[3-(5-acetamidopyridinyl)]-3-buten- 1-amine and (E)-N-methyl-4-[3-(5-carbamoylpyridinyl)]-3-buten-1-amine. These compounds may be produced according to the techniques set forth in C.V. Greco et al., *J Heterocyclic Chem.* 7(4):761 (1970). More specifically, the commercially available starting material, 5-bromonicotinic acid is converted to both 5-bromonicotinamide and 3-amino-5-bromopyridine. The 3-amino-5-bromopyridine can be acylated with acetic anhydride to give 3-acetamido-5-bromopyridine. 3-Acetamido-5-bromopyridine may then be reacted with N-methyl-N-(tert-butoxycarbonyl)-3-buten-1-amine (prepared according to the preceeding techniques) using the Heck reaction described hereinabove and set forth in W.C. Frank et al.,*J. Org. Chem.* 43(15):2947 (1978). The reaction gives (E)-N-methyl-N-(tert-butoxycarbonyl)-4-[3-(5-acetamidopyridinyl)]-3-buten-1-amine. The Heck reaction of 5-bromonicotinic acid with N-methyl-N-(tert-butoxycarbonyl)-3-buten-1-amine gives (E)-N-methyl-N-(tert-butoxycarbonyl)-4-[3-(5-carbamoylpyridinyl)]-3-buten-1-amine. The treatment of either product withaqueous acid effects the removal of the tert-butoxycarbonyl groups from these compounds, giving the 5-acetamido and 5-carbamoyl substituted metanicotinic compounds respectively.

The present invention relates to a method for providing treatment of conditions of the vascular or circulatory system, particularly in regions of microcirculation, which conditions are associated with decreased blood flow, particularly in the microvasculature. In particular, the method comprises administering to a subject in need of treatment, an amount of a compound effective for providing some degree of prevention of the progression of the condition (i.e., provide protective effects), amelioration of the symptoms of the condition, and amelioration of the reoccurrence of the condition. The method involves administering an effective amount of a compound selected from the general formula set forth hereinbefore. The present invention also relates to a pharmaceutical composition incorporating a compound selected from the general formula set forth hereinbefore. The compounds normally are not optically active. However, certain compounds can possess substituent groups of a character so that those compounds possess optical activity. Optically active compounds can be employed as racemic mixtures or as enantiomers.

The compounds can be employed in a free base form or in a salt form (e.g., as pharmaceutically acceptable salts). Examples of suitable pharmaceutically acceptable salts include inorganic acid addition salts such as hydrochloride, hydrobromide, sulfate, phosphate, and nitrate; organic acid addition salts such as acetate, propionate, succinate, lactate, glycolate, malate, tartrate, citrate, maleate, fumarate, methansulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates.

The pharmaceutical composition also can include various other components as additives or adjuncts. Exemplary pharmaceutically acceptable components or adjuncts which are employed in relevant circumstances include antioxidants, free radical scavenging agents, peptides, growth factors, antibiotics, bacteriostatic agents, immunosuppressives, anticoagulents, buffering agents, anti-inflammatory agents, anti-pyretics, time release binders, anaesthetics, steroids and corticosteroids. Such components can provide additional therapeutic benefit, act to affect the therapeutic action of the pharmaceutical composition, or act towards preventing any potential side effects which may be posed as a result of administration of the pharmaceutical composition.

The manner in which the compounds are administered can vary. Although it is possible to administer the compound in the form of a bulk active chemical, it is preferred to present the compound in the form of a pharmaceutical composition or formulation for parenteral administration. As such, a preferred pharmaceutical composition includes the compound as an active ingredient, and a pharmaceutically acceptable carrier. Typically, the pharmaceutical composition is administered as an aqueous or non-aqueous solution, as a suspension, or as an emulsion in a pharmaceutically acceptable liquid or mixture of liquids. The compound within the pharmaceutical composition is administered internally by injection or intravenously. For example, the pharmaceutical composition can be administered intravenously as an infusion (e.g., within aqueous dextrose or saline solutions). Exemplary methods for administering such compounds (e.g., so as to achieve sterile or aseptic conditions) will be apparent to the skilled artisan. In certain circumstances administration can be through spinal injection. Certain methods suitable for administering compounds useful according to the present invention are set forth in Goodman and Gilman's *The Pharmacological Basis of Therapeutics*, 6th Edit. (1980). Alternatively, the compounds can be administered by inhalation (e.g., in the form of an aerosol either nasally or using delivery articles of the type set forth in U.S. Pat. No. 4,922,901 to Brooks et al.); topically (e.g., in lotion form); orally (e.g., in liquid form within a solvent such as an aqueous or non-aqueous liquid, or within a solid carrier as a tablet or capsule); or transdermally (e.g., using a transdermal patch). Exemplary methods for administering such compounds will be apparent to the skilled artisan. For example, the compounds can be administered in the form of a tablet, a hard gelatin capsule or as a time release capsule. As another example, the compounds can be delivered transdermally using the types of patch technologies available from Ciba-Geigy Corporation and Alza Corporation. The administration to the patient can be intermittent; or at a gradual, continuous, constant or controlled rate. Administration can be to a warm-blooded animal (e.g., a mammal, such as a mouse, rat, cat, rabbit, dog, pig, cow, or monkey); and advantageously to a human being. The frequency of administration varies from patient to patient. Administration preferably is such so as to optimize the effect upon the $\beta 2$-containing receptor subtypes while minimizing the effects upon receptors which do not contain $\beta 2$ receptor subtypes.

Compounds of the present invention are selective to $\beta 2$-containing nicotinic acetylcholine receptors (e.g., receptors sub-types containing $\beta 2$ subunits). Grady et al., *J Neurochem.* 59:848 (1992). See, Boulter et al., *Proc. Natl. Acad Sci. U.S.A.* 84:7763 (1987); Deneris et al., *Neuron* 1:45 (1988); Flores et al., *Mol. Pharmacol.* 45:212 (1994); Deneris et al., *Trends Pharmacol. Sci.* 12:34 (1991); Goldman et al., *Cell* 48:965 (1987); and Luetje et al., *J. Neursci.* 55:837 (1991). By this is meant that the compounds of the present invention bind to relevant receptors and, are relatively potent (i.e., effect relevant receptor sub-types at low concentrations), and are relatively efficacious (i.e., significantly affect relevant receptor sub- types by activating those receptor sub-types to a high degree). Concentrations, determined as the amount of compound per volume of receptor-containing tissue, typically provide a measure of the degree to which that compound binds to and affects relevant receptor sub-types. The compounds of the present invention are selective in that at relevant concentrations (i.e., low concentrations) those compounds bind to, and have an affect upon, receptor sub-types containing $\beta$-2 subunits; however, the compounds are not sufficiently potent to affect certain other receptor sub-types (e.g., those $\beta 1$-containing receptor subtypes and $\beta$-4-containing receptor sub-types which do not possess $\beta 2$ subunits) to any significant degree.

Compounds of the present invention, by selectively binding to and affecting $\beta 2$-containing receptor sub-types, are capable of having the effect of reversing vasoconstriction and inducing vasodilation in relevant tissues, in instances when increased blood flow is desired. As such, the compounds have the ability to interact with nicotinic receptors subtypes, such as those present in afferent nerve terminals, and have the ability to elicit the release of neurotransmitters and/or biologically active local humoral neuromediators, thereby providing effects which cause a net vasodilation of arteries and capillaries, resulting in increased blood flow. However, the amount of compound capable of providing effective improvement of blood flow, particularly in regions of microcirculation, typically is not sufficient to elicit any appreciable effect upon relevant receptor sub-types which may in turn cause diminished blood flow. As such, administration of compounds of the present invention provides a therapeutic window in which treatment of conditions of the microvasculature characterized by decreased blood flow is provided, and effects resulting from vasoconstriction are avoided.

Certain nicotinic compounds do not exhibit selectivity between receptor sub-types to any significant degree. Thus, upon administration of certain nicotinic compounds in relevant amounts (e.g., in amounts sufficient to bind to and affect $\beta 2$-containing receptor sub-types to a significant degree) those nicotinic compounds simultaneously affect other receptor sub-types to a significant degree. As a result, such effects upon the various receptor sub-types may alter both vasoconstriction and vasodilation, and hence a net increase in vasodilation (i.e., net improvement in blood flow) may not occur. However, the concentration of certain nicotinic compounds which are administered can vary, and can be controlled to some degree by manner of delivery (e.g., injection of compound as opposed to time release delivery, as with transdermal patch). However, controlled manner of delivery to certain non-selective nicotinic receptor subtypes does not necessarily provide a suitably wide therapeutic window for efficient treatment.

The dose of the compound is that amount effective to prevent re-occurrence of the symptoms of the condition being prevented, or to treat some symptoms of the condition from which the patient suffers. By "effective amount", "therapeutic amount" or "effective dose" is meant an amount sufficient to elicit the desired pharmacological or therapeutic effects, thus enhancing vasodilation and resulting in effective prevention or treatment of the condition characterized by the decreased blood flow. Prevention of the disorder is manifested by a delaying of the onset of the symptoms of the condition. Treatment of the condition is manifested by a decrease in the symptoms associated with the condition or an amelioration of the reoccurrence of the symptoms of the condition.

The effective dose can vary, depending upon factors such as the condition of the patient, the severity of the symptoms experienced by the patient, and the manner in which the pharmaceutical composition is administered. For human patients, the effective dose of typical compounds generally requires administering the compound in an amount of at least about 1, often at least about 10, and frequently at least about 25 mg/24 hr./patient. For human patients, the effective dose of typical compounds requires administering the compound which generally does not exceed about 500, often does not exceed about 400, and frequently does not exceed about 300 mg/24 hr./patient. In addition, administration of the effective dose is such that the concentration of the compound within the plasma of the patient normally does not exceed 500 ng/ml, and frequently does not exceed 100 ng/ml.

The compounds useful according to the method of the present invention have the ability to interact with certain nicotinic cholinergic receptors in the body of the patient (i.e., the compounds interact selectively with β2-containing receptor subtypes). As such these compound have the ability to express nicotinic pharmacology, and in particular, to act as nicotinic agonists. The receptor binding constants of typical compounds useful in carrying out the present invention generally exceed about 1 nM, often exceed about 5 nM, and frequently exceed about 10 nM. The receptor binding constants of such typical compounds generally are less than about 1000 nM, often are less than about 500 nM, and frequently are less than about 100 nrM. Receptor binding constants provide a measure of the ability of the compound to bind to relevant receptor sites of certain cells of the patient. See, Cheng, et al., *Biochem. Pharmacol.* 22:3099 (1973).

The compounds useful according to the method of the present invention have the ability to demonstrate a nicotinic pharmacology as evidenced by their ability to elicit neurotransmitter secretion from nerve ending preparations (i.e., synaptosomes). As such, these compounds have the ability to cause relevant neurons to release or secrete acetylcholine, dopamine, or other neurotransmitters. Generally, the compounds useful in carrying out the present invention provide for the secretion of neurotransmitters in amounts of at least about 10 percent, often at least about 50 percent, and frequently at least about 75 percent, of that elicited by an equal molar amount of (S)-(−)-nicotine. Certain compounds of the present invention can provide secretion of dopamine in an amount which can exceed that elicited by an equal molar amount of (S)-(−)-nicotine.

The compounds of the present invention, when employed in effective amounts in accordance with the method of the present invention, essentially lack the ability to elicit activation to any significant degree, of nicotinic receptor subtypes which do not contain β2 subunits. Luther et al., *J. Neurochem* 9:1082 (1989); Lukas, *Mol Cell. Neurosci.* 4:1 (1989); and Oswald et al., *Neurosci. Lett.* 96:207 (1989). For example, the compounds lack the ability to elicit activation receptors of human muscle to any significant degree. In that regard, the compounds of the present invention demonstrate poor ability to cause isotopic rubidium ion flux through nicotinic receptors in cell preparations derived from muscle preparations. See, Lukas et al., *Anal. Biochem.* 175:212 (1988). Thus, such compounds exhibit receptor activation constants or $EC_{50}$ values (i.e., which provide a measure of the concentration of compound needed to activate half of the relevant receptor sites of the skeletal muscle of a patient) which are relatively high. Generally, typical compounds activate isotopic rubidium ion flux by less than 20 percent, often by less than 15 percent, frequently by less than 10 percent, and even less than 5 percent of that elicited by an equal molar amount of (S)-(−)-nicotine. Certain compounds elicit essentially no activation of muscle receptor subtypes.

Because the compounds of the present invention essentially lack the ability to activate to any significant degree, receptors which do not include β2-subunits, the compounds of the present invention are also essentially ineffective in eliciting activation of certain ganglionic-type nicotinic receptors. As such, the compounds of the present invention have poor ability to cause isotopic rubidium ion flux through nicotinic receptors in cell preparations derived from the adrenal gland. See, Lukas *J. Pharmacol. Exp. Ther.* 251:175 (1989); Rogers et al., J. Neurosci. 12:4611 (1992); and Whiting et al., *Mol. Brain Res.* 10:61 (1990). Typical ganglionic receptors include α3β4 receptor subtypes, (i.e., non-β2 containing receptor subtypes). Generally, the compounds useful in the present invention activate isotopic rubidium ion flux by less than 25 percent, often by less than 15 percent, frequently by less than 10 percent, and even less than 5 percent of that elicited by an equal molar amount of (S)-(−)-nicotine. Certain compounds elicit essentially no activation of ganglionic receptor subtypes.

Compounds of the present invention, when employed in effective amounts in accordance with the method of the present invention, are effective towards providing some degree of treatment of conditions of the vascular system, which conditions are associated with restricted blood flow or vasoconstriction, amelioration of the symptoms of such conditions, and amelioration to some degree of the reoccurrence of certain conditions. An effective dose of a compound of the present invention is sufficient to provide the desired effects upon the circulatory system, but is insufficient (i.e., is not at a high enough concentration) to provide undesirable side effects, such as side effects which may be caused by the interaction of the compounds of the present invention with receptors subtypes which do not contain β2 subunits. Preferably, effective administration of a compound of the present invention resulting in treatment of a condition of the vascular system occurs upon administration of less than ⅕, and often less than ¹⁄₁₀, that amount sufficient to cause any side effects to a significant degree.

The following examples are provided to illustrate the present invention, and should not be construed as limiting thereof. In these examples, all parts and percentages are by weight, unless otherwise noted.

EXAMPLE 1

Sample No. 1 is (E)-N-methyl-4[3-(6-methylpyridin)yl]-3-buten-1-amine monofumarate, which was prepared essentially in accordance with the techniques described in U.S. Pat. No. 5,597,919 to Dull et al., the subject matter of which is already incorporated herein by reference in its entirety.

EXAMPLE 2

Sample No. 2 is (E)-4(5-pyrimidinyl)-3-buten-1-amine, which was prepared using the techniques described in U.S. Pat. No. 5,597,919 to Dull et al., the subject matter of which is already incorporated herein in its entirety.

EXAMPLE 3

Sample No. 3 is (E)-N-Methyl-4-[3-(5-phenylpyridin)yl] -3-buten- 1-amine, which is prepared according to the following procedure.

3-Bromo-5-phenylpyridine: A mixture of 3,5-dibromopyridine (15.00 g, 63.3 mmol), phenylboronic acid (8.11 g, 66.5 mmol), sodium carbonate (14.09 g, 133.0 mmol), water (100 mL), toluene (400 mL), absolute ethanol (100 mL), and tetrakis(triphenylphosphine)palladium(0) (3.66 g, 3.17 mmol) was stirred and heated under reflux at 92° C. (oil bath temperature) for 19 h. The mixture was cooled to ambient temperature and extracted with dichloromethane (400 mL). The dichloromethane layer was washed with saturated, aqueous $NaHCO_3$ solution, dried ($Na_2SO_4$), filtered, and concentrated to a residue. Vacuum distillation using a short-path apparatus produced 10.58 g of a white solid, bp 70°–110° C. at 0.05 mm Hg (lit. bp 100°–101° C. at ~0.1 mm Hg, see U.S. Pat. No. 5,409,920 to Guthikonda. Further purification by column chromatography on silica gel, eluting with hexane-ethyl acetate (5:1, v/v) afforded 8.23 g (55.5%) of 3-bromo-5-phenylpyridine as a white solid, mp 45°–46° C., $R_f$ 0.50 (hexane-ethyl acetate (5:1, v/v)).

$^1$H NMR (CDCl$_3$, 300 MHz): δ 8.74 (1H, d, J=1.7 Hz), 8.64 (1H, d, J=1.9 Hz), 8.01 (1H, t, J=2.0 Hz), 7.56–7.38 (5H, m). $^{13}$C NMR (CDCl$_3$, 75 MHz): δ 149.35, 146.38, 138.27, 136.86, 136.31, 129.20, 128.69, 127.18, 120.91. HRMS: Calcd. for C$_{11}$H$_8$BrN (M$^+$): m/z 232.984010. Found: 232.984177.

(E)-4-[3-(5-Phenylpyridin)yl]-3-buten-1-ol: Under a nitrogen atmosphere, a mixture of 3-buten-1-ol (476 mg, 6.6 mmol), 3-bromo-5-phenylpyridine (1.50 g, 6.4 mmol), palladium(II) acetate (14.4 mg, 0.064 mmol), tri-o-tolylphosphine (78.0 mg, 0.256 mmol), triethylamine (2.5 mL), and acetonitrile (5.0 mL) was stirred and heated under reflux at 90° C. (oil bath temperature) for 18 h. Upon cooling to ambient temperature, the mixture was diluted with water (25 mL) and extracted with dichloromethane (4×25 mL). The combined dichloromethane extracts were washed with water (25 mL), dried (Na$_2$SO$_4$), filtered, and concentrated by rotary evaporation to give a dark-green oil (1.69 g). Vacuum distillation using a test-tube apparatus gave 873 mg of a yellow oil, bp 60°–80° C. at 0.05 mm Hg. Further purification by column chromatography on silica gel (60 g), eluting in succession with hexane-ethyl acetate (5:1, v/v), hexane-ethyl acetate (1:1, v/v), and ethyl acetate afforded 604 mg (41.8%) of (E)-4-[3-(5-phenylpyridin)yl]-3-buten-1-ol as a yellow oil, $R_f$ 0.27 (ethyl acetate).

$^1$H NMR (CDCl$_3$, 300 MHz): δ 8.66 (1H, d, J=2.0 Hz), 8.54 (1H, d, J=1.9 Hz), 7.83 (1H, t, J=2.1 Hz), 7.58–7.54 (2H, m), 7.49–7.36 (3H, m), 6.54 (1H, d, J=15.9 Hz), 6.38 (1H, dt, J=15.9, 6.9 Hz), 3.80 (2H, t, J=6.3 Hz), 2.53 (2H, dq, J=6.3, 1.2 Hz), 1.78 (1H, br s).

(E)-N-Methyl-4-[3-(5-phenylpyridin)yl]-3-buten-1-amine: Under a nitrogen atmosphere, a cold (0° C.), stirring solution of (E)-4-[3-(5-phenylpyridin)yl]-3-buten-1-ol (577 mg, 2.56 mmol), anhydrous dichloromethane (4 mL), and pyridine (1 drop) was treated with p-toluenesulfonyl chloride (537 mg, 2.82 mmol). The mixture was allowed to warm to ambient temperature. After stirring 17 h, the solution was concentrated by rotary evaporation, and the residue was further dried under high vacuum. The resulting brown gum was dissolved in tetrahydrofuran (5 mL) and 40% aqueous methylamine (5 mL) was added. The solution was stirred 6 h at ambient temperature and was then concentrated by rotary evaporation to a brown gum. The residue was partitioned between 1M NaOH solution (10 mL) and chloroform (10 mL). The aqueous phase was separated and extracted with chloroform (2×10 mL). The combined chloroform extracts were washed with water (10 mL), dried (Na$_2$SO$_4$), filtered, and concentrated by rotary evaporation to give a dark-brown residue. To purify the product, water (25 mL) was added to the residue, and the pH was adjusted to 8.2 with 30% HCl solution. The resulting solution was extracted with dichloromethane (2×10 mL); the dichloromethane extracts were subsequently discarded following thin layer chromatography analysis on silica gel. The pH of the aqueous phase was raised to 12.5 using 30% NaOH solution; the product was extracted with tert-butyl methyl ether (3×10 mL). The combined tert-butyl methyl ether extracts were washed with water (10 mL), dried (Na$_2$SO$_4$), filtered, and concentrated by rotary evaporation to give 589 mg of a dark-brown oil. Purification by column chromatography on silica gel, eluting with ethyl acetate produced 95.1 mg of (E)-4-[3-(5-phenylpyridin)yl]-3-buten-1-ol. Subsequent elution with methanol-ammonium hydroxide (9:1, v/v) afforded 82.3 mg (13.5%) of (E)-N-methyl-4-[3-(5-phenylpyridin)yl]-3-buten-1-amine as a dark-brown oil.

$^1$H NMR (CD$_3$OD 300 MHz): δ 8.63 (1, br s), 8.52 (1H, br s), 8.11 (1H, t, J=1.9 Hz), 7.69–7.65 (2H, m), 7.53–7.40 (3H, m), 6.65 (1d, J=16.0 Hz), 6.52 (1H, dt, J=15.9, 6.7 Hz), 2.89 (2H, t, J=6.7 Hz), 2.59–2.49 (2H, m), 2.52 (3H, s). MS (ESI): m/z 239 (M+H)$^{30}$ HRMS: Calcd. for C$_{16}$H$_{18}$N$_2$ (M$^+$): m/z 238.146999. Found: 238.146600.

EXAMPLE 4

Sample No. 4 is (E)-4-[3-(5-methoxypyridin)yl]-3-buten-1-amine monofumarate, which was prepared essentially in accordance with the techniques described in U.S. Pat. No. 5,597,919 to Dull et al., the subject matter of which is already incorporated herein by reference.

EXAMPLE 5

Sample No. 5 is (E)-N-methyl-4-[3-(5-aminopyridin)yl]-3-buten-1-amine, which was prepared according to the techniques described in U.S. Pat. No. 5,597,919 to Dull et al., the subject matter of which is already incorporated by reference.

EXAMPLE 6

Sample No. 6 is (E)-N-Methyl-4-[3-(5-benzyloxypyridin)yl]-3-buten-1-amine, which was prepared according to the following procedure.

3-Bromo-5-benzyloxvpyridine: Under a nitrogen atmosphere, small pieces of sodium (1.48 g, 64.4 mmol) were added to benzyl alcohol (17.11 g, 158.0 mmol), and the mixture was stirred and heated at 70° C. for 18 h. To the stirring, viscous mixture was added 3,5-dibromopyridine (5.00 g, 21.1 mmol), copper powder (255 mg, 4.0 mmol), and benzyl alcohol (15 mL). The mixture was further heated at 100° C. for 48 h. The reaction mixture was allowed to cool to ambient temperature, diluted with water (50 mL), and extracted with diethyl ether (5×50 mL). The combined ether extracts were dried (Na$_2$SO$_4$), filtered, and concentrated by rotary evaporation. Vacuum distillation removed excess benzyl alcohol, bp 68°–72° C. at 2.6 mm Hg. Further vacuum distillation afforded 3.17 g (38.0%) of 3-bromo-5-benzyloxypyridine as a white, crystalline solid, mp 64°–66° C.

$^1$H NMR (CDCl$_3$, 300 MHz): δ 8.28 (2H, m), 7.42–7.34 (6H, m), 5.08 (2H, s).

$^{13}$C NMR (CDCl$_3$, 75 MHz): δ 155.20, 143.21, 136.71, 135.44, 128.79, 128.55, 127.55, 126.97, 124.37, 70.65.

HRMS: Calcd. for C$_{12}$H$_{10}$BrNO (M$^+$): m/z 262.994575. Found: 262.995321.

(E)-4-[3-(5-Benzyloxyvyridin)yl]-3-buten-1-ol: Under a nitrogen atmosphere, a mixture of 3-buten-1-ol (151 mg, 2.1 mmol), 3-bromo-5-benzyloxypyridine (528 mg, 2.0 mmol), palladium(II) acetate (5 mg, 0.02 mmol), tri-o-tolylphosphine (25 mg, 0.08 mmol), triethylamine (0.5 mL), and acetonitrile (1.0 mL) was stirred and heated under reflux for 20 h. Upon cooling, the mixture was diluted with water (10 mL) and extracted with dichloromethane (2×10 mL). The combined dichloromethane extracts were dried (Na$_2$SO$_4$), filtered, and concentrated by rotary evaporation to give a dark-yellow oil (527 mg). Purification by column chromatography on silica gel, eluting with 2.5% (v/v) methanol in ethyl acetate afforded 387 mg (75.8%) of (E)-4-[3-(5-benzyloxypyridin)yl]-3-buten-1-ol as a colorless gum.

¹H NMR (CDCl₃, 300 MHz): δ 8.21 (1H, d, J=2.7 Hz), 8.18 (1H, d, J=1.6 Hz), 7.41–7.33 (5H, m), 7.25 (1H, s), 6.44 (1H, d, J=15.9 Hz), 6.27 (1H, dt, J=16.0, 7.0 Hz), 5.09 (2H, s), 3.77 (2H, t, J=6.2 Hz), 2.44 (2H, dq, J=6.2, 1.0 Hz), 1.67 (1, br s).

(E)-N-Methyl-4-[3-(5-benzyloxypyridin)yl]-3-buten-1-amine: Under a nitrogen atmosphere, a cold (0° C.), stirring solution of (E)-4-[3-(5-benzyloxypyridin)yl]-3-buten-1-ol (368 mg, 1.44 mmol), dichloromethane (1.5 mL), and pyridine (1 drop) was treated with p-toluenesulfonyl chloride (302 mg, 1.58 mmol). The mixture was allowed to warm to ambient temperature. After stirring for 16 h, the solution was concentrated under a stream of nitrogen, and the residue was further dried under high vacuum. The resulting residue was dissolved in tetrahydrofuran (3 mL), and 40% aqueous methylamine (3 mL) was added. The solution was stirred 6 h at ambient temperature and was then concentrated by rotary evaporation to a dark gum. The residue was partitioned between 1M NaOH solution (10 mL) and chloroform (10 mL). The chloroform layer was separated, washed with water (10 mL), dried (Na₂SO₄), filtered, and concentrated by rotary evaporation to give a dark-brown oil (445 mg). The product was purified by column chromatography on silica gel, eluting with 2.5% (v/v) triethylamine in methanol to give 162 mg (41.9%) of (E)-N-methyl-4-[3-(5-benzyloxypyridin)yl]-3-buten-1-amine as a light-yellow oil.

¹H NMR (CDCl₃, 300 MHz): δ 8.20 (1H, d, J=2.7 Hz), 8.17 (1H, d, J=1.8 Hz), 7.43–7.33 (5H, m), 7.22 (1H, m), 6.40 (1, d, J=15.9 Hz), 6.24 (1H, dt, J=15.9, 6.9 Hz), 5.09 (2H, s), 2.72 (2H, t, J=6.8 Hz), 2.46–2.39 (2H, m), 2.44 (3H, s), 1.76 (1H, br s).

¹³C NMR (CDCl₃, 75 MHz): δ 154.92, 140.88, 136.73, 136.17, 133.70, 131.03, 128.71, 128.29, 127.91, 127.53, 117.93, 70.32, 51.03, 36.29, 33.47.

HRMS: Calcd. for $C_{17}H_{20}N_2O$ $(M^{+)}$: $^{m/z}$ 268.157563. Found: 268.157420.

EXAMPLE 7

Sample No. 7 is (E-N-methyl-4-[3–5-bromopyridin)yl]-3-buten-1-amine monofumarate, which was prepared essentially in accordance with the techniques described in U.S. Pat. No. 5,597,919 to Dull et al., already incorporated herein by reference.

EXAMPLE 8

Sample No. 8 is (E)-N-methyl-4-[3-(5-methoxypyridin)yl]-3-butene-1-amine which is prepared according to the techniques described in U.S. patent application Ser. No. 08/631,762 the subject matter of which is incorporated herein by reference in its entirety.

EXAMPLE 9

Sample No. 9 is (E)-N-methyl-4-[3-(5-ethoxypyridin)-yl]-3-butene-1-amine which is prepared according to the techniques described in U.S. patent application Ser. No. 08/631,762 the subject matter of which is already incorporated herein by reference in its entirety.

EXAMPLE 10

Sample No. 10 is (E)-N-methyl-5-(3-pyridinyl)-4-penten-2-amine which is prepared according to the techniques described in U.S. patent application Ser. No. 08/631,762 the subject matter of which is already incorporated herein by reference in its entirety.

EXAMPLE 11

Sample No. 11 is (E)-N-methyl-4-(5-pyrimidinyl)-3-buten-1-amine which is prepared according to the techniques described in U.S. Pat. No. 5,597,919 to Dull et al., the subject matter of which is already incorporated herein in its entirety.

EXAMPLE 12

Sample No. 12 is (Z)-metanicotine monofumarate which is prepared according to the techniques described in U.S. Pat. No. 5,597,919 to Dull et al., the subject matter of which is already incorporated herein in its entirety.

EXAMPLE 13

Sample No. 13 is (E)-4-[3-(5-Bromopyridin)yl]-3-buten-1-amine Hemifumarate, which was prepared according to the following techniques.

N-3-Buten-1-phthalimide was prepared essentially in accordance with the techniques described in W. C. Frank, et al., *J. Org Chem.* 43:2947 (1978).

(E)-N-4-[3-(5-Bromopyridin)yl]-3-buten-1-phthalimide: Under a nitrogen atmosphere, a mixture of N-3-buten-1-phthalimide (8.74 g, 43.5 mmol), 3,5-dibromopyridine (10.00 g, 42.2 mmol), palladium(II) acetate (190 mg, 0.84 mmol), tri-o-tolylphosphine (514 mg, 1.69 mmol), and triethylamine (8.55 g, 84.4 mmol) was stirred at 100°–107° C. (oil bath temperature) for 48 h. Upon cooling to ambient temperature, the brown residue was filtered, washed with water (200 mL), and dissolved in hot N,N-dimethylformamide (45 mL). The resulting solution was filtered through Celite® filter aid. Water (50 mL) was added to the filtrate, and the mixture was cooled at 5° C. for 18 h. The resulting solids were filtered, washed with cold water, followed by cold 2-propanol (10 mL), and vacuum dried at 50° C. to give a yellowish brown semisolid (13.69 g). The product was recrystallized twice from toluene (40 mL), filtered, washed with cold toluene (5 mL) and cold 2-propanol (5 mL), and vacuum dried at 50° C. to give 2.11 g (14.0%) of (E)-N-4-[3-(5- bromopyridin)yl]-3-buten-1-phthalimide as a light beige powder, mp 145- 148° C.

¹H NMR (CDCl₃): δ 8.46 (lH, d, J=2.0 Hz), 8.37 (1H, d, J=1.8 Hz), 7.82 (2H, m), 7.74 (1H, t, J=2.0 Hz), 7.69 (2H, m), 6.33 (2H, d, J=15.9 Hz), 6.25 (1H, dt, J=15.9, 5.9 Hz), 3.84 (2H, t, J=6.9 Hz), 2.62 (2H, m).

(E)-4-[3-(5-Bromopyridin)yl]-3-buten-1-amine: Under a nitrogen atmosphere, a solution of (E)-N-4-[3-(5-bromopyridin)yl]-3 -buten-1-phthalimide (2.16 g, 6.1 mmol), hydrazine hydrate (0.91 g, 18.2 mmol), methanol (40 mL) and chloroform (80 mL) was allowed to stir for 5 h at ambient temperature. The reaction was monitored by thin layer chromatography on silica gel (chloroform-methanol (99:1, v/v)). Additional hydrazine hydrate (0.45 g, 9.1 mmol) was added to the reaction mixture which was stirred at ambient temperature for a total of 45 h. The thick mixture was poured into 1M NaOH solution (750 mL), stirred 30 min at ambient temperature, and extracted with chloroform (3×100, 2×200 mL). The combined chloroform extracts were dried (Na₂SO₄), filtered, and concentrated by rotary evaporation. Further drying under vacuum at ambient temperature afforded a golden oil (1.11 g). Purification by vacuum distillation produced 0.57 g of a light-yellow oil, bp 109° C. at 0.05 mm Hg. Further purification by vacuum distillation afforded 180 mg (13.1%) of (E)-4-[3-(5-bromopyridin)yl]-3-buten-1-amine as a light-yellow oil, bp 108°–115° C. at 0.03 mm Hg.

¹H NMR (CD₃OD): δ 8.49 (1H, d, J=1.8 Hz), 8.45 (1H, d, J=2.2 Hz), 8.09 (1H, t, J=2.1 Hz), 6.48 (2H, m), 2.82 (2H, t, J=7.0 Hz), 2.43 (2H, m). EI-MS: m/z (relative intensity) 227 (M⁻, 0.1%).

(E)-4-[3-(5-Bromopyridin)yl]-3-buten-1-amine Hemifumarate: (E)-4-[3-(5-Bromopyridin)yl]-3-buten-1-amine (173 mg, 0.76 mmol) in a small volume of 2-propanol, was added to a warm solution of fumaric acid (95.6 mg, 0.82 mmol) in 2-propanol. The white mixture was concentrated by rotary evaporation, and the solids were recrystallized from 2-propanol. The mixture was kept at 5° C. for 18 h. The resulting solids were filtered, washed with cold 2-propanol, cold diethyl ether, and dried under vacuum at 50° C. to yield a light-beige powder. A second recrystallization from 2-propanol afforded 103 mg (47.4% yield) of (E)-4-[3-(5-bromopyridin)yl]-3-buten-1-amine hemifumarate as a cream-colored powder, mp 175°–176.5° C.

¹H NMR (D₂O, 300 MHz): δ 8.51 (1H, s), 8.47 (1H, s), 8.12 (1H, s), 6.59 (1H, d, J=16.0 Hz), 6.51 (1, s), 6.39 (1H, dt, J=16.0, 7.0 Hz), 3.20 (2H, t, J=7.0 Hz), 2.65 (2H, q, J=7.0 Hz).

¹³C NMR (D₂O, 75 MHz): δ 174.62, 148.36, 145.32, 136.50, 135.32, 134.73, 129.24, 128.42, 120.64, 38.67, 30.30.

Analysis calculated for $C_9H_{11}BrN_2 \cdot 0.5\ C_4H_4O_4$: C, 46.33; H, 4.59; Br, 28.03; N, 9.83. Found: C, 46.20; H, 4.71; Br, 27.92; N, 9.75.

EXAMPLE 14

Sample No. 14 is (E)-metanicotine monofumarate which is prepared essentially according to the techniques described in Laforge, *J.A.C.S.* 50:2477 (1928).

EXAMPLE 15

Sample No. 15 is (E)-N-Methyl-4-[3-(5-phenoxypyridin)yl]-3-buten-1-amine, which was prepared according to the following techniques.

3-Bromo-5-phenoxypyridine: Sodium phenoxide trihydrate (7.50 g, 44.1 mmol) was dried under vacuum at 65° C. for 18 h at 0.6 mm Hg to yield 5.08 g of sodium phenoxide. Under a nitrogen atmosphere, 3,5-dibromopyridine (4.00 g, 16.9 mmol) and anhydrous N,N-dimethylformamide (40 mL) were added to the sodium phenoxide (5.08 g, 43.8 mmol). The resulting mixture was stirred at 110° C. for 44 h. After cooling to ambient temperature, water (75 mL) was added, and the pH was adjusted to 13.0 using 30% NaOH solution. The solution was extracted with diethyl ether (4×60 mL). The combined ether extracts were washed with saturated NaCl solution (50 mL), dried (NaSO₄), filtered and concentrated by rotary evaporation to a brown oil (4.0 g). The oil was vacuum distilled, collecting a forerun (317 mg), bp 48°–65° C. at 0.05 mm Hg. Further distillation afforded 3.35 g (79.8%) of 3-bromo-5-phenoxypyridine as a pale-yellow oil, bp 75°–112° C. at 0.05 mm Hg (lit. bp 110°–115° C. at 1.7 mm Hg, see K. Fujikawa, et al. *Agr. Biol. Chem.* 34:68 (1970).

¹H NMR (CDCl₃, 300 MHz): δ 8.39 (1H, d, J=1.7 Hz), 8.31 (1H, d, J=2.3 Hz), 7.42–7.35 (3H, m), 7.22–7.17 (1H, m), 7.05–7.01 (2H, m).

(E)-4-[3-(5-Phenoxypyridin)yl]-3-buten-1-ol: Under a nitrogen atmosphere, a mixture of 3-bromo-5-phenoxypyridine (1.80 g, 7.23 mmol), palladium(II) acetate (15 mg, 0.067 mmol), tri-o-tolylphosphine (80.9 mg, 0.266 mmol), 3-buten-1-ol (494 mg, 6.85 mmol), triethylamine (2.5 mL), and acetonitrile (5 mL) was stirred and heated under reflux for 22 h. The reaction was monitored by thin layer chromatography on silica gel eluting with chloroform-methanol (98:2, v/v). Additional palladium(II) acetate (7.5 mg) and tri-o-tolylphosphine (44 mg) were added to the reaction mixture, which was stirred and heated under reflux for an additional 2 h. After cooling to ambient temperature, the mixture was diluted with water (20 mL) and extracted with dichloromethane (3×25 mL). The combined organic layers were washed with water (25 mL), dried (NaSO₄), filtered, and concentrated to yield a dark-yellow oil (1.85 g). The product was purified by column chromatography on silica gel, eluting with chloroform-methanol (94:6, v/v). Selected fractions were combined and concentrated. Purification by vacuum distillation gave 0.468 g of (E)-4-[3-(5-phenoxypyridin)yl]-3-buten-1-ol as a viscous, yellow oil, bp 155°–175° C. at 0.15 mm Hg. Further distillation produced an additional 1.270 g of product as a viscous, yellow oil, bp 165°–175° C. at 0.15 mm Hg, for a total yield of 1.738 g (100%).

¹H NMR (CD₂Cl₂, 300 MHz): δ 8.31 (1H, d, J=1.5 Hz), 8.20 (1H, d, J=2.4 Hz), 7.41–7.34 (2H, m), 7.29 (1H, t, J=2.2 Hz), 7.17 (1H, m), 7.04 (2H, m), 6.45 (1H, d, J=16.0 Hz), 6.27 (1H, dt, J=15.9, 7.0 Hz), 3.72 (2H, t, J=6.3 Hz), 2.46 (2H, m), 1.58 (1H, br s).

(E)-N-Methyl-4-[3-(5-phenoxypyridin)yl]-3-buten-1-amine: Under a nitrogen atmosphere, methanesulfonyl chloride (0.66 g, 5.8 mmol) was added dropwise to a stirring, ice-cold solution of (E)-4-[3-(5-phenoxypyridin)yl]-3-buten-1-ol (1.27 g, 5.3 mmol), triethylamine (1.07 g, 10.5 mmol), and tetrahydrofuran (15 mL). The mixture was stirred for 48 h at ambient temperature. The dark-brown mixture was diluted with water (50 mL) and extracted with chloroform (3×50 mL). The combined chloroform extracts were dried (Na₂SO₄), filtered, and concentrated to a gold oil (0.873 g). Aqueous methylamine (20 mL, 40% solution) was added to the oil, and the mixture was allowed to stir at ambient temperature for 18 h. The solution was basified with 30% NaOH solution to pH 11–12 and extracted with diethyl ether (4×25 mL). The combined ether extracts were dried (Na₂SO₄), filtered, and concentrated to a yellow syrup. To purify the product, water (50 mL) was added to the residue, and the pH was adjusted to ~8.0 with 30% HCl solution. The resulting solution was extracted with dichloromethane (50 mL). The aqueous layer was separated, the pH was adjusted to 12.5 using 30% NaOH solution, and this alkaline solution was extracted with tert-butyl methyl ether (3×25 mL). Thin layer chromatography analysis on silica gel, eluting with methanol-ammonium hydroxide (10:1, v/v) indicated that the spent dichloromethane layer contained some product. Therefore, water (25 mL) was added to the dichloromethane extract, and the pH was adjusted to 8.0. The aqueous phase was separated, the pH was adjusted to pH 12.5 using 30% NaOH solution, and this solution was extracted with tert-butyl methyl ether (2×25 mL). All tert-butyl methyl ether layers were combined, dried (NaSO₄), filtered, and concentrated to yield 106.5 mg (8.0%) of (E)-N-methyl-4-[3-(5-phenoxypyridin)yl]-3-buten-1-amine as a dark-gold oil.

¹H NMR (CD₂Cl₂, 300 MHz): δ 8.30 (1H, d, J=1.8 Hz), 8.18 (1H, d, J=2.7 Hz), 7.38 (2H, m), 7.28 (1H, t, J=2.2 Hz), 7.16 (1H, m), 7.06–7.02 (2H, m), 6.41 (1H, d, J=16.0 Hz), 6.27 (1H, dt, J=16.0, 6.7 Hz), 2.69 (1, t, J=6.8 Hz), 2.40 (3H, s), 2.42–2.35 (2H, m), 1.60 (1H, br s).

¹³C NMR (CD₂Cl₂, 75 MHz): δ 156.96, 154.27, 143.19, 140.14, 134.59, 131.77, 130.39, 127.86, 124.36, 122.09, 119.30, 51.03, 35.85, 33.20.

HRMS: Calcd. for $C_{16}H_{18}N_2O$ (M⁺): m/z 254.141913. Found: 254.142750.

EXAMPLE 16

Sample No. 16 is (E)-N-Methyl-4-[3-(5-isopropoxypyridin)yl]-3-buten-1-amine, which is prepared according to the following procedure.

3-Bromo-5-isoproipoxypyridine: Under a nitrogen atmosphere, 2-propanol (30 mL) was added to potassium (2.4 g, 61.4 mmol) at 0° C., and the mixture was stirred at 0° C. for 30 min. To the resulting solution was added 3,5-dibromopyridine (4.74 g, 20.0 mmol) and copper powder (250 mg, 3.9 mmol). The mixture was heated under reflux under a nitrogen atmosphere for 70 h. Upon cooling to ambient temperature, the mixture was concentrated under high vacuum to a solid, which was diluted with water (200 mL) and extracted with diethyl ether (3×150 mL). The combined ether extracts were dried ($Na_2SO_4$), filtered, and concentrated by rotary evaporation to a dark-brown oil (3.71 g). Purification by column chromatography on silica gel, eluting with 10→20% (v/v) diethyl ether in benzene afforded 1.38 g (31.9%) of 3-bromo-5-isopropoxypyridine as a volatile, colorless oil.

$^1$H NMR ($CDCl_3$, 300 MHz): δ 8.23 (1H, s), 8.19 (1, s), 7.31 (1H, t, J=2.1 Hz), 4.54 (1H, septet, J=6.0 Hz), 1.34 (6H, d, J=6.0 Hz).

(E)-4-[3-(5-Isopropoxypyridin)yl]-3-buten-1-ol: Under a nitrogen atmosphere, a mixture of 3-buten-1-ol (296 mg, 4.1 mmol), 3-bromo-5-isopropoxypyridine (864 mg, 4.0 mmol), palladium(II) acetate (9.0 mg, 0.04 mmol), tri-o-tolylphosphine (50.0 mg, 0.16 mmol), triethylamine (1.0 mL), and acetonitrile (2.0 mL) was stirred and heated under reflux for 27 h. Upon cooling to ambient temperature, the mixture was diluted with water (20 mL) and extracted with dichloromethane (2×20 mL). The combined dichloromethane extracts were dried ($Na_2SO_4$), filtered, and concentrated by rotary evaporation to give an orange oil (843 mg). Purification by column chromatography on silica gel, eluting with 0→4% (v/v) methanol in ethyl acetate afforded 498 mg (60.1%) of (E)-4-[3-(5-isopropoxypyridin)yl]-3-buten-1-ol as a thick, light-yellow oil.

$^1$H NMR ($CDCl_3$, 300 MHz): δ 8.13 (1H, d, J=1.4 Hz), 8.10 (1H, d, J=2.6 Hz), 7.14 (1H, t, J=2.3 Hz), 6.43 (1, d, J=16.0 Hz), 6.26 (1H, dt, J=15.9, 7.0 Hz), 4.57 (1H, septet, J=6.0 Hz), 3.76 (2H, t, J=6.2 Hz), 2.49 (2H, dq, J=6.1, 1.2 Hz), 1.66 (1H, br s), 1.33 (6H, d, J=5.9 Hz).

(E)-N-Methyl-4-[3-(5-isopropoxypyridin)yl]-3-buten-1-amine: Under a nitrogen atmosphere, a cold (0° C.), stirring solution of (E)-4-[3-(5-isopropoxypyridin)yl]-3-buten-1-ol (466 mg, 2.25 mmol), anhydrous dichloromethane (2 mL), and pyridine (2 drops) was treated with p-toluenesulfonyl chloride (540 mg, 2.83 mmol). The mixture was allowed to warm to ambient temperature. After stirring 16 h, the solution was concentrated under a stream of nitrogen, and the residue was further dried under high vacuum. The residue was dissolved in N,N-dimethylformamide (5 mL), and a solution of 2N methylamine in tetrahydrofuran (5 mL) was added. After stirring under a nitrogen atmosphere for 24 h at ambient temperature, the solution was diluted with water (25 mL) and extracted with diethyl ether (2×30 mL). The combined ether extracts were washed with water (10 mL) and saturated NaCl solution (20 mL), dried ($Na_2SO_4$), filtered, and concentrated by rotary evaporation to a residue (470 mg). Purification by column chromatography on silica gel, eluting with 2.5% (v/v) triethylamine in absolute ethanol afforded 153 mg (30.9%) of (E)-N-methyl-4-[3-(5-isopropoxypyridin)yl]-3-buten-1-amine as a reddish, amber oil.

$^1$H NMR ($CDCl_3$, 300 MHz): δ 8.13 (1, d, J=1.7 Hz), 8.10 (1H, d, J=2.7 Hz), 7.13 (1H, t, J=2.1 Hz), 6.40 (1H, d, J=16.0 Hz), 6.23 (1, dt, J=15.9, 6.9 Hz), 4.57 (1H, septet, J=6.1 Hz), 2.73 (2H, t, J=6.9 Hz), 2.46–2.40 (2H, m), 2.45 (3H, s), 2.19 (1H, br s), 1.33 (6H, d, J=6.0 Hz).

$^{13}$C NMR ($CDCl_3$, 75 MHz): 67 154.09, 140.41, 137.77, 133.67, 130.56, 128.17, 119.05, 70.62, 50.90, 36.06, 33.26, 21.94.

HRMS: Calcd. for $C_{13}H_{20}N_2O$ ($M^+$): $^{m/z}$ 220.157563. Found: 220.157686.

EXAMPLE 17

Sample No. 17 is (E)-N-Methyl-4-[3-(5-methoxymethylpyridin)yl]-3-buten-1-amine, which is prepared according to the following procedure.

3-Bromo-5-methoxymethvlpyridine: Under a nitrogen atmosphere, a solution of 5-bromonicotinic acid (5.05 g, 25.0 mmol) and thionyl chloride (10 mL) was stirred and heated. The excess thionyl chloride was removed by distillation, and the residue was dried briefly under high vacuum. To the resulting light-yellow solid in dry tetrahydrofuran (40 mL) was added sodium borohydride (1.90 g, 50.0 mmol) at 0° C. under a nitrogen atmosphere. The mixture was stirred 1 h at 0° C. and allowed to warm to ambient temperature. The mixture was added to a cold, saturated aqueous $NH_4Cl$ solution (100 mL) and extracted with diethyl ether (3×50 mL). The combined ether extracts were dried ($Na_2SO_4$), filtered, and concentrated by rotary evaporation to a semisolid (2.77 g). Thin layer chromatography analysis on silica gel indicated mostly 5-bromonicotinic acid; therefore the semisolid was partitioned between ether and saturated aqueous $NaHCO_3$ solution. The ether layer was separated and concentrated by rotary evaporation to a residue (0.75 g). Purification by column chromatography on silica gel, eluting with ethyl acetate-hexane (1:1, v/v) afforded 379 mg (8.1%) of 3-bromo-5-hydroxymethylpyridine.

Under a nitrogen atmosphere, a solution of 3-bromo-5-hydroxymethylpyridine (379 mg, 2.0 mmol) in dry tetrahydrofuran (10 mL) was treated at ambient temperature with sodium hydride (160 mg, 4.0 mmol, 60% dispersion in mineral oil). After stirring 5 min at ambient temperature, the opaque, yellow mixture was treated with methyl iodide (342 mg, 2.4 mmol). After stirring 2 h at ambient temperature, the mixture was added to cold water (30 mL) and extracted with diethyl ether (3×20 mL). The combined ether extracts were dried ($Na_2SO_4$), filtered, and concentrated by rotary evaporation to an orange oil (429 mg). Purification by column chromatography on silica gel, eluting with 15% (v/v) ethyl acetate in hexane afforded 266 mg (65.3%) of 3-bromo-5-methoxymethylpyridine as a colorless oil.

$^1$H NMR ($CDCl_3$, 300 MHz): δ 8.59 (1H, d, J 2.0 Hz), 8.45 (1, s), 7.83 (1, m), 4.43 (2H, s), 3.40 (3H, s).

(E)-4-[3-(5-Methoxymethylpyridin)yl]-3-buten-1-ol: Under a nitrogen atmosphere, a mixture of 3-buten-1-ol (108 mg, 1.5 mmol), 3-bromo-5-methoxymethylpyridine (240 mg, 1.2 mmol), palladium(II) acetate (5.0 mg, 0.02 mmol), tri-o-tolylphosphine (25.0 mg, 0.08 mmol), triethylamine (0.5 mL), and acetonitrile (1.0 mL) was stirred and heated under reflux for 21 h. Upon cooling to ambient temperature, the mixture was diluted with water (10 mL) and extracted with dichloromethane (2×10 mL). The combined dichloromethane extracts were dried ($Na_2SO_4$), filtered, and concentrated by rotary evaporation to an oil (240 mg). Purification by column chromatography on silica gel, eluting with 0→4% (v/v) methanol in ethyl acetate afforded 148 mg (64.5%) of (E)-4-[3-(5-methoxymethylpyridin)yl]-3-buten-1-ol as an oil.

¹H NMR (CDCl₃, 300 MHz): δ 8.47 (iH, d, J=1.8 Hz), 8.37 (1H, d, J=1.6 Hz), 7.66 (1H, t, J=2.1 Hz), 6.47 (1H, d, J=16.0 Hz), 6.32 (1H, dt, J=16.0, 6.9 Hz), 4.44 (2H, s), 3.77 (2H, t, J=6.2 Hz), 3.39 (3H, s), 2.50 (2H, dq, J=6.3, 1.2 Hz), 1.66 (1H, br s).

(E)-N-Methyl-4-r3-(5-methoxymethylpyridin)yl]-3-buten- 1 -amine: Under a nitrogen atmosphere, a cold (0° C.), stirring solution of (E)-4-[3-(5-methoxymethylpyridin) yl]-3-buten-1-ol (140 mg, 0.72 mmol), anhydrous dichloromethane (1 mL), and pyridine (1 drop) was treated with p-toluenesulfonyl chloride (172 mg, 0.90 mmol). The mixture was allowed to warm to ambient temperature. After stirring 12 h, the solution was concentrated under a stream of nitrogen, and the residue was further dried under high vacuum. The residue was dissolved in N,N-dimethylformamide (2 mL) and treated with 40% aqueous methylamine solution (1 mL) at 0° C. After stirring under a nitrogen atmosphere for 7 h at ambient temperature, the solution was added to 1M NaOH solution (10 mL) and extracted with diethyl ether (2×10 mL). The combined ether extracts were dried (Na₂SO₄), filtered, and concentrated by rotary evaporation to a residue (99 mg). Purification by column chromatography on silica gel, eluting with 2.5% (v/v) triethylamine in methanol afforded 24 mg (16.1%) of (E)-N-methyl-4-[3-(5-methoxymethylpyridin)yl]-3-buten-1-amine as a light-yellow oil.

¹H NMR (CDCl₃, 300 MHz): δ 8.47 (1H, d, J=2.1 Hz), 8.37 (1H, d, J=1.9 Hz), 7.65 (1H, t, J=2.0 Hz), 6.43 (1H, d, J=16.0 Hz), 6.29 (1H, dt, J=16.0, 6.7 Hz), 4.44 (2H, s), 3.39 (3H, s), 2.73 (2H, t, J=6.9 Hz), 2.45 (3H, s), 2.43 (2H, m), 1.56 (1H, br s).

¹³C NMR (CDCl₃, 75 MHz): δ 147.54, 147.50, 133.29, 132.88, 131.82, 131.08, 127.88, 72.08, 58.39, 51.14, 36.36, 33.56.

HRMS: Calcd. for C₁₂H₁₈N₂O (M⁻)⁺ $^{m/z}$ 206.141913. Found: 206.142612.

EXAMPLE 18

Sample No. 18 is (E)-4-(3-pyridinyl)-3-buten-1-amine difumarate, which is prepared according to the following techniques.

(E)-4-(3-Pyridinyl)-3-buten-1-amine: This compound was prepared essentially in accordance with the techniques described in W. Frank, et al., *J. Org. Chem.* 43:2947 (1978).

(E)-4-(3-Pyridinyl)-3-buten- l-amine Difumarate:

(E)-4-(3-pyridinyl)-3-buten-1-amine was converted to its difumarate, mp 164.5°–167° C.

¹H NMR (DMSO-d₆, 300 MHz): δ 8.70 (1H, d), 8.52 (1H, d), 7.94 (1H, d), 7.45 (1H, dd), 6.65 (4H, s), 6.63 (1H, d), 6.49 (1H, dt), 2.96 (2H, t), 2.52 (2H, m).

¹³C NMR (DMSO-d₆, 75 MHz): δ 167.2, 148.3, 147.7, 134.7, 132.6, 132.5, 128.7, 128.4, 123.7, 38.2, 30.5.

EXAMPLE 19

Sample No. 19 is (E)-N-Methyl-4-[3-(5-ethoxypyridin)yl]-3-buten-1-amine sesquifumarate, which is prepared according to the following procedure.

(E)-N-Methyl-4-[3-(5-ethoxypyridin)yl]-3-buten-1-amine is prepared in accordance with the techniques set forth in U.S. patent application Ser. No. 08/631,762.

Under a nitrogen atmosphere, fumaric acid (165 mg, 1.18 mmol) was added to a solution of (E)-N-methyl-4-[3-(5-ethoxypyridin)yl]-3-buten-1-amine (244 mg, 1.18 mmol) in 2-propanol (15 mL). After stirring 30 min at ambient temperature, the solution was concentrated by rotary evaporation to a light-brown solid. The solid was dissolved in a mixture of 2-propanol (6 mL) and ethanol (1 mL), assisted by warming. The resulting solution was treated with decolorizing carbon, filtered, and cooled at −20° C. for 5 days. The crystalline solids were filtered, collected, and dissolved in a mixture of ethanol (3 mL) and methanol (1 mL). This solution was filtered through a sintered glass funnel to remove insoluble matter, and the filtrate was diluted with 2-propanol (4 mL) and cooled at −20° C. The crystalline solids were collected and dried under high vacuum to give 102 mg (26.8%) of (E)-N-methyl-4-[3-(5-ethoxypyridin)-yl]-3-buten-1-amine sesquifumarate as a light-tan, crystalline powder, mp 126°–127° C.

¹H NMR (D₂O, 300 MHz): δ 8.33 (1, br s), 8.26 (1H, d, J=2.4 Hz), 7.97 (1, t, J=2.1 Hz), 6.68 (1, d , J=16.1 Hz), 6.62 (2H, s), 6.52 (1H, dt, J=16.1, 7.0 Hz), 4.27 (2H, q, J=6.9 Hz), 3.24 (2H, t, J=7.0 Hz), 2.74 (3H, s), 2.70 (2H, m), 1.44 (3H, t, J=7.0 Hz).

¹³C NMR (D₂O, 75 MHz): δ 175.36, 159.89, 139.88, 137.87, 136.28, 134.56, 132.20, 130.30, 129.07, 68.96, 50.81, 35.73, 32.17, 16.58.

Anal. Calcd for C₁₂H₁₈N₂O . 1.5 C₄H₄O₄: C, 56.83; H, 6.36; N, 7.37. Found: C, 56.88; H, 6.43; N, 7.34.

COMPARISON EXAMPLE

For comparison purposes, Sample No. C-1 is provided. This sample is (S)-(−)-nicotine, which has been reported to have demonstrated affinity to bind to numerous nicotinic acetylcholine receptor subtypes including β2-subunits.

EXAMPLE 20

Determination of Binding to Relevant Receptor Sites

Binding of the compounds to relevant receptor sites was determined in accordance with the techniques described in U.S. Pat. No. 5,597,919 to Dull et al., the subject matter of which is already incorporated herein by reference in its entirety. Inhibition constants (Ki values), reported in nM, were calculated from the IC₅₀ values using the method of Cheng et al., *Biochem, Pharmacol.* 22:3099 (1973). Data are presented in Table I.

EXAMPLE 21

Determination of Dopamine Release

Dopamine release was measured using the techniques described in U.S. Pat. No. 5,597,919 to Dull et al., the subject matter of which is already incorporated herein by reference in its entirety. Release is expressed as a percentage of release obtained with a concentration of (S)-(−)-nicotine resulting in maximal effects. Reported EC₅₀ is expressed in nM and E$_{max}$ represents the amount released relative to nicotine. Data are presented in Table I.

EXAMPLE 22

Determination of Interaction with Muscle

The determination of the interaction of the compounds with muscle receptors was carried out in accordance with the techniques described in U.S. Pat. No. 5,597,919 to Dull et al., the subject matter of which is already incorporated herein by reference in its entirety. The muscle tissues employed are representative of those which are believed absent of receptor subtypes containing β2-subunits. The maximal activation for individual compounds ($E_{max}$) was determined as a percentage of the maximal activation induced by (S)-(−)-nicotine. Data are presented in Table I.

EXAMPLE 23

Determination of Interaction with Ganglia

The determination of the interaction of the compounds with ganglionic receptors was carried out in accordance with the techniques described in U.S. Pat. No. 5,597,919 to Dull et al., the subject matter of which is already incorporated herein by reference in its entirety. The ganglionic tissues employed are representative of those which are believed absent of receptor subtypes containing β2-subunits. The maximal activation for individual compounds (Emax) was determined as a percentage of the maximal activation induced by (S)-(−)-nicotine. Data are presented in Table I.

TABLE I

| Sample No. | Ki (nM) | Dopamine Release $E_{max}$ | $EC_{50}$ (nM) | Muscle Effect (% nicotine) | Ganglion Effect (% nicotine) |
|---|---|---|---|---|---|
| C-1 | 2 | 100 | 115 | 100 | 100 |
| 1 | 176 | 115 | 10000 | 2 | 4 |
| 2 | 269 | 113 | 4360 | 0 | 0 |
| 3 | 184 | >160 | >100,000 | 8 | 0 |
| 4 | 150 | 95 | 3800 | 0 | 0 |
| 5 | 658 | 85 | 2000 | 4 | 4 |
| 6 | 5 | 33 | 4000 | 12 | 0 |
| 7 | 79 | 107 | 2400 | 8 | 11 |
| 8 | 10 | 103 | 191 | 0 | 0 |
| 9 | 9 | 124 | 287 | 0 | 0 |
| 10 | 82 | 182 | 21400 | 4 | 6 |
| 11 | 85 | 77 | 5800 | 12 | 0 |
| 12 | 511 | 96 | 8307 | 0 | 0 |
| 13 | 707 | 29 | 49 | 5 | 0 |
| 14 | 25 | 90 | 1022 | 0 | 0 |
| 15 | 21 | 14 | 114 | 5 | <15 |
| 16 | 6 | 57 | 51 | 8 | <15 |
| 17 | 130 | 46 | 16,000 | 13 | 0 |
| 18 | 119 | 81 | 5020 | 15 | 23 |
| 19 | 5 | 70 | 276 | 3 | <15 |

*Sample C-1 is a control and is not an example of the invention

The data in Table I indicate that the compounds of the present invention have the capability of binding to α4β2 receptor subtypes, as evidenced by their low Ki values. The data also show that the compounds have the capability of activating β2-containing receptor subtypes, as evidenced by their ability to release dopamine. Thus, the data indicate that such compounds have known nicotinic pharmacology, particularly at the β2-containing nicotinic acetylcholine receptor subtype. The data also indicate that the compounds do not cause appreciable effects at muscle or ganglia receptors, which subtypes are absent of β2 subunits. Thus, the data indicate that the compounds, are being selective to receptor subtypes containing β2 subunits. Thus, the compounds are useful in providing a net increase in vasodilation relative to vasoconstriction, and hence are useful for providing increased blood flow. The compounds are useful in treating conditions within the vascular or circulatory system, particularly in regions of microcirculation.

The foregoing is illustrative of the present invention and is not to be construed as limiting thereof. The invention is defined by the following claims, with equivalents of the claims to be included therein.

That which is claimed is:

1. A method for treating a condition characterized by restricted blood flow, said method comprising administering to a subject in need thereof, an effective amount of an aryl substituted olefinic amine compound in an amount sufficient to selectively bind to and affect nicotinic cholinergic receptor subtypes containing β2 subunits.

2. The method according to claim 1, wherein said compound has the formula:

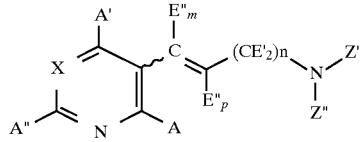

wherein X is nitrogen or carbon bonded to a substituent species characterized as having a sigma m value between −0.3 and 0.75; n is an integer which ranges from 1 to 7; E' is hydrogen or $C_1$–$C_5$ alkyl or halo substituted $C_1$–$C_5$ alkyl; E" is $C_1$–$C_5$ alkyl or halo substituted $C_1$–$C_5$ alkyl; Z' and Z" are each individually selected form the group consisting of hydrogen, $C_1$–$C_5$ alkyl, aryl rings, and can form a ring structure,

A, A' and A" are each individually selected from the group consisting of hydrogen, $C_1$–$C_7$ alkyl, and halo; m is 0 or 1; p is 0 or 1; with the proviso that when m or p or both are 0 then that E" is hydrogen the wavy line in the structure represents a cis (Z) or trans (E) form of the compound.

3. The method according to claim 1, wherein the condition being treated or prevented is Raynaud's phenomenon.

4. The method according to claim 1, wherein the condition being treated or prevented is Raynaud's disease.

5. The method according to claim 1, wherein the condition being treated or prevented is decreased blood flow in regions of microcirculation following surgery.

6. The method according to claim 1, wherein the condition being treated or prevented is decreased blood flow in regions of microcirculation of a digit following reattachment thereof.

7. The method according to claim 1, wherein the compound of Formula I is (Z)-metanicotine.

8. The method according to claim 1, wherein the compound of Formula I is (E)-metanicotine.

9. The method according to claim 1, wherein the compound of Formula I is (E)-N-methyl-4-[3-(5-benzyloxypyridin)yl]-3-buten-1-amine.

10. The method according to claim 1, wherein the compound of Formula I is (E)-4-[3-(5-bromopyridin)yl]-3-buten-1-amine hemifumarate.

11. The method according to claim 1, wherein the compound of Formula I is (E)-N-methyl-4-[3-(5-phenoxypyridin)yl]-3-buten-1-amine.

12. The method according to claim 1 wherein the compound of Formula I is (E)-N-methyl-4-[3-(5-isopropoxypyridin)yl]-3-buten-1-amine.

13. The method according to claim 1, wherein the compound of Formula I is (E)-N-methyl-4-[3-(5-methoxymethylpyridin)yl]-3-buten-1-amine.

14. The method according to claim 1, wherein the compound of Formula I is (E)-N-methyl-4-[3-(5-phenylpyridin)yl]-3-buten-1-amine.

15. The method according to claim 1, wherein the compound of Formula I is (E)-4-(3-pyridinyl)-3-buten-1-amine.

16. The method according to claim 1, wherein the compound of Formula I is (E)-N-methyl-4-[3-(5-ethoxypyridin)yl]-3-buten-1-amine sesquifumarate.

17. The method according to claim 1, wherein the amount effective to treat said condition is at least about 25 mg/patient/24 hours and does not exceed about 500 mg/patient/24 hours.

18. The method according to claim 1, wherein the amount effective to treat said condition is at least about 10 g/patient/24 hours and does not exceed about 400 g/patient/24 hours.

19. The method according to claim 1, wherein the amount of the compound administered is such that the subject does not experience a concentration of compound in plasma which exceeds 500 ng/ml.

20. The method according to claim 1, wherein X is nitrogen or carbon bonded to a substituent species characterized as having a sigma m value greater than 0; n is an integer which ranges from 1 to 3; Z' and Z" individually represent hydrogen, methyl or isopropyl; A and A' represent hydrogen; A" represents hydrogen, methyl or ethyl; m is 0, and p is 0.

21. The method according to claim 1, wherein X is nitrogen or carbon bonded to a substituent species characterized as having a sigma m value less than 0; n is an integer which ranges from 1 to 3; Z' and Z" individually represent hydrogen, methyl or isopropyl; A and A' represent hydrogen; A" represents hydrogen, methyl or ethyl; m is 0 and p is 0.

22. The method according to claim 1, wherein X is nitrogen or carbon bonded to a substituent species characterized as having a sigma m value between about −0.25 and about 0.6; n is an integer which ranges from 1 to 3; Z' and Z" individually represent hydrogen, methyl or isopropyl; A and A' represent hydrogen; A" represents hydrogen, methyl or ethyl; m is 0 and p is 0.

23. The method according to claim 1, wherein X is nitrogen; n is an integer which ranges from 1 to 3; Z' and Z" individually represent hydrogen, methyl or isopropyl; A and A' represent hydrogen; A" represents hydrogen, methyl or ethyl; m is 0 and p is 0.

24. A method for providing vasodilation, said method comprising administering to a subject suffering from the effects of vasoconstriction, an effective amount of an aryl substituted olefinic amine compound in an amount sufficient to selectively bind to and affect nicotinic cholingergic receptor subtypes containing β2 subunits.

25. The method according to claim 24, wherein said compound has the formula:

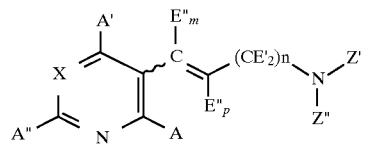

wherein X is nitrogen or carbon bonded to a substituent species characterized as having a sigma m value between −0.3 and 0.75; n is an integer which ranges from 1 to 7; E' is hydrogen or $C_1$–$C_5$ alkyl or halo substituted $C_1$–$C_5$ alkyl; E" is $C_1$–$C_5$ alkyl or halo substituted $C_1$–$C_5$ alkyl; Z' and Z" are each individually selected form the group consisting of hydrogen, $C_1$–$C_5$ alkyl, aryl rings, and can form a ring structure

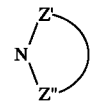

A, A' and A" are each individually selected from the group consisting of hydrogen, $C_1$–$C_7$ alkyl, and halo; m is 0 or 1; p is 0 or 1 with the proviso that when m or p or both are 0 then that E" is hydrogen; the wavy line in the structure represents a cis (Z) or trans (E) form of the compound.

26. The method according to claim 24, wherein the condition being treated or prevented is Raynaud's phenomenon.

27. The method according to claim 24, wherein the condition being treated or prevented is Raynaud's disease.

28. The method according to claim 24, wherein the condition being treated or prevented is decreased blood flow in regions of microcirculation following surgery.

29. The method according to claim 24, wherein the condition being treated or prevented is decreased blood flow in regions of microcirculation of a digit following reattachment thereof.

30. The method according to claim 24, wherein the compound of Formula I is (Z)-metanicotine.

31. The method according to claim 24, wherein the compound of Formula I is (E)-metanicotine.

32. The method according to claim 24, wherein the compound of Formula I is (E)-N-methyl-4-[3-(5-benzyloxypyridin)yl]-3-buten-1-amine.

33. The method according to claim 24, wherein the compound of Formula I is (E)-4-[3-(5-bromopyridin)yl]-3-buten-1-amine hemifumarate.

34. The method according to claim 24, wherein the compound of Formula I is (E)-N-methyl-4-[3-(5-phenoxypyridin)yl]-3-buten-1-amine.

35. The method according to claim 24, wherein the compound of Formula I is (E)-N-methyl-4-[3-(5-isopropoxypyridin)yl]-3-buten-1-amine.

36. The method according to claim 24, wherein the compound of Formula I is (E)-N-methyl-4-[3-(5-methoxymethylpyridin)yl]-3-buten-1-amine.

37. The method according to claim 24, wherein the compound of Formula I is (E)-N-methyl-4-[3-(5-phenylpyridin)yl]-3-buten-1-amine.

38. The method according to claim 24, wherein the compound of Formula I is (E)-4-(3-pyridinyl)-3-buten-1-amine.

39. The method according to claim 24, wherein the compound of Formula I is (E)-N-methyl-4-[3-(5-ethoxypyridin)yl]-3-buten-1-amine sesquifumarate.

40. The method according to claim 24, wherein the amount effective to provide vasodilation is at least about 25 mg/patient/24 hours and does not exceed about 500 mg/patient/24 hours.

41. The method according to claim 24, wherein the amount effective to provide vasodilation is at least about 10 g/patient/24 hours and does not exceed about 400 g/patient/24 hours.

42. The method according to claim 24, wherein the amount of the compound administered is such that the subject does not experience a concentration of compound in plasma which exceeds 500 ng/ml.

43. The method according to claim 24, wherein X is nitrogen or carbon bonded to a substituent species characterized as having a sigma m value greater than 0; n is an integer which ranges from 1 to 3; Z' and Z" individually represent hydrogen, methyl or isopropyl; A and A' represent hydrogen; A" represents hydrogen, methyl or ethyl; m is 0 and p is 0.

44. The method according to claim 24, wherein X is nitrogen or carbon bonded to a substituent species characterized as having a sigma m value less than 0; n is an integer which ranges from 1 to 3; Z' and Z" individually represent hydrogen, methyl or isopropyl; A and A' represent hydrogen; A" represents hydrogen, methyl or ethyl; m is 0 and p is 0.

45. The method according to claim 24, wherein X is nitrogen or carbon bonded to a substituent species characterized as having a sigma m value between about −0.25 and about 0.6; n is an integer which ranges from 1 to 3; Z' and Z" individually represent hydrogen, methyl or isopropyl; A and A' represent hydrogen; A" represents hydrogen, methyl or ethyl; m is 0 and p is 0.

46. The method according to claim 25, wherein X is nitrogen; n is an integer which ranges from 1 to 3; Z' and Z" individually represent hydrogen, methyl or isopropyl; A and A' represent hydrogen; A" represents hydrogen, methyl or ethyl; m is 0 and p is 0.

\* \* \* \* \*